United States Patent
Chang et al.

(10) Patent No.: US 6,527,704 B1
(45) Date of Patent: Mar. 4, 2003

(54) ENDOSCOPIC CAMERA SYSTEM INTEGRATED WITH A TROCAR SLEEVE

(75) Inventors: William H. L. Chang, Milpitas, CA (US); Markus Yap, Santa Clara, CA (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 09/266,251

(22) Filed: Mar. 10, 1999

(51) Int. Cl.[7] .................................................. A61B 1/00
(52) U.S. Cl. ..................... 600/112; 600/121; 600/138; 604/264
(58) Field of Search .................... 600/112, 114, 600/121, 138, 188, 125; 604/264

(56) References Cited

U.S. PATENT DOCUMENTS

| | | | | |
|---|---|---|---|---|
| 3,945,375 A | * | 3/1976 | Banko | 600/104 |
| 5,313,962 A | * | 5/1994 | Obenchain | 128/898 |
| 5,676,682 A | | 10/1997 | Yoon | |
| 5,800,451 A | | 9/1998 | Buess et al. | |
| 5,902,231 A | * | 5/1999 | Foley et al. | 600/102 |
| 5,928,137 A | * | 7/1999 | Green | 600/104 |

FOREIGN PATENT DOCUMENTS

DE 196 20 887 A1 * 11/1997 .......... A61B/17/34

OTHER PUBLICATIONS

Brochure, "System Solutions for Arthroscopy", Stryker Endoscopy, Santa Clara, CA, 2 pages.
Brochure, "The Stryker Model 882TE Camera", Strkyer Endoscopy, Santa Clara, CA, 6 pages.

* cited by examiner

*Primary Examiner*—John Mulcahy
(74) *Attorney, Agent, or Firm*—Blakely, Sokoloff, Taylor & Zafman LLP; Jordan M. Becker

(57) ABSTRACT

A trocar sleeve capable of holding an endoscopic camera system and an associated endoscopic camera system are provided. When integrated with the trocar sleeve, the endoscopic camera can be used to provide a panoramic overview of the surgical area to supplement the view provided by a main endoscopic camera. The trocar sleeve includes a tube and a base coupled to the tube. The tube includes a channel for accommodating a surgical tool, such as a trocar. The tube further includes a receptacle separate from the channel, for allowing removable attachment of an endoscope to the trocar sleeve. The base includes a fastener for allowing removable attachment of an endoscopic camera head to the trocar sleeve. The camera head has a corresponding fastener for mating with the fastener of the base.

15 Claims, 9 Drawing Sheets

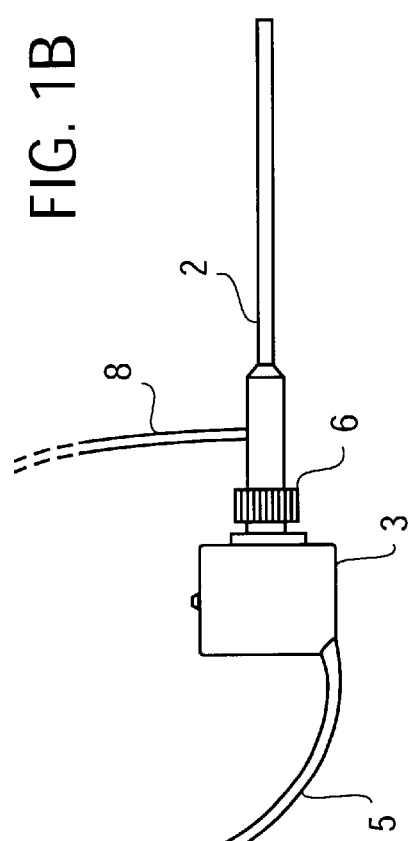
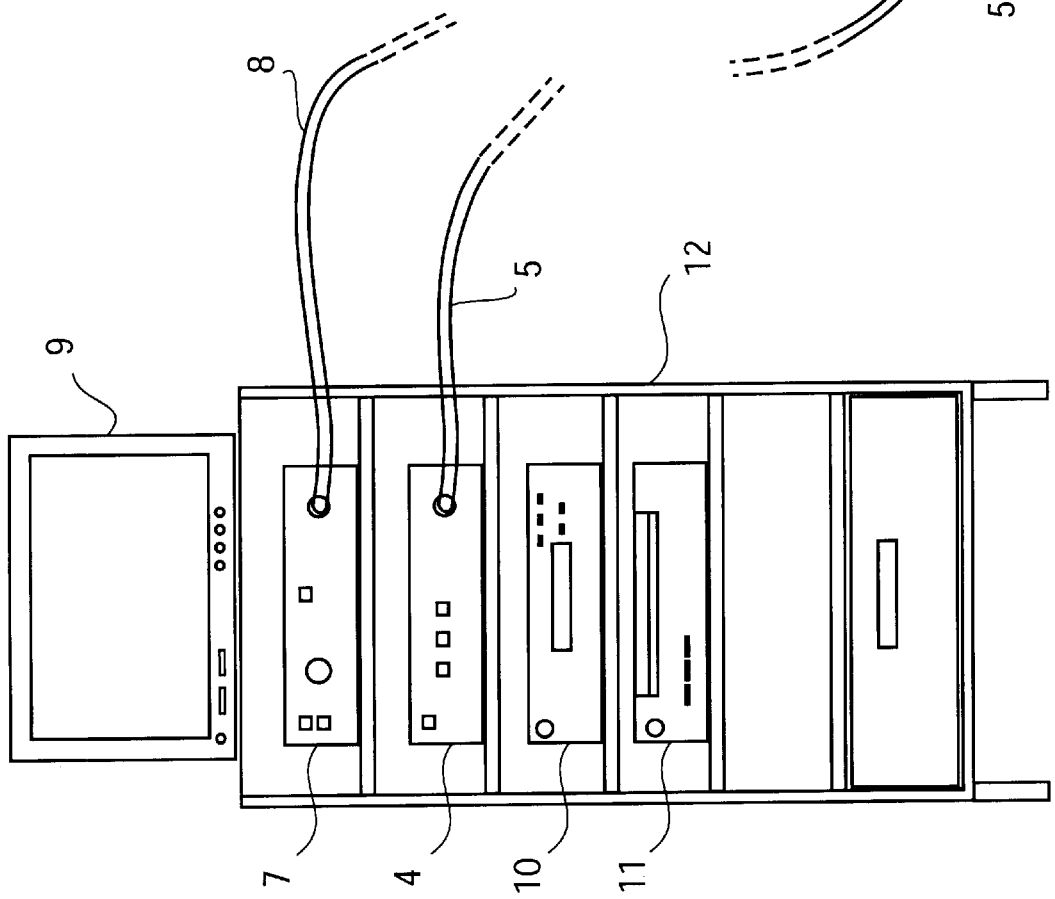

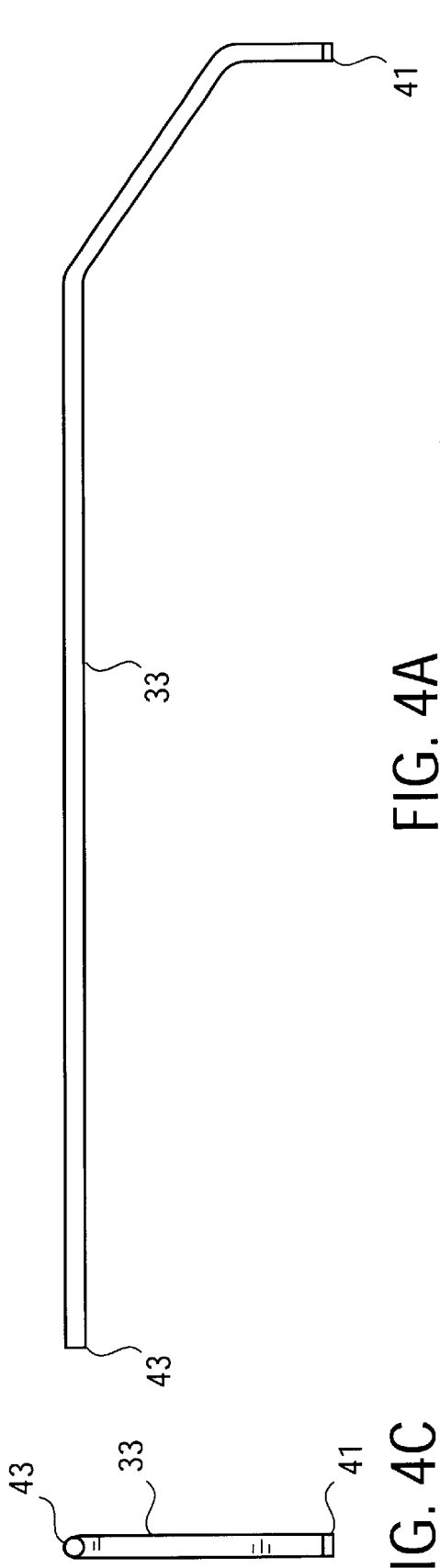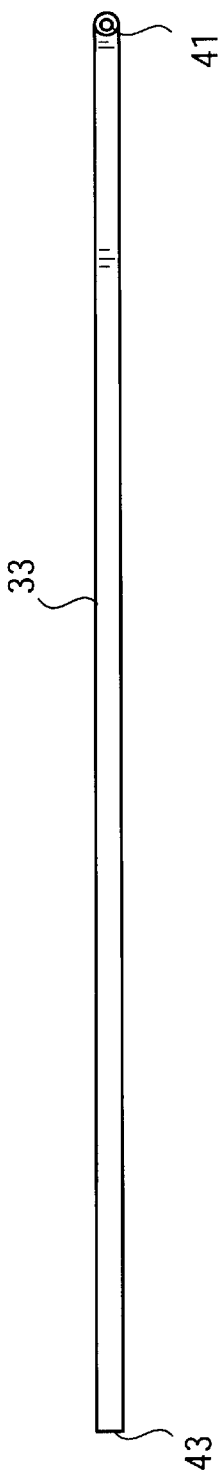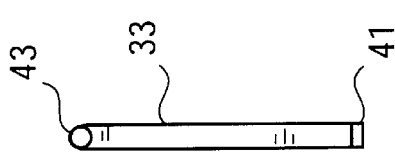

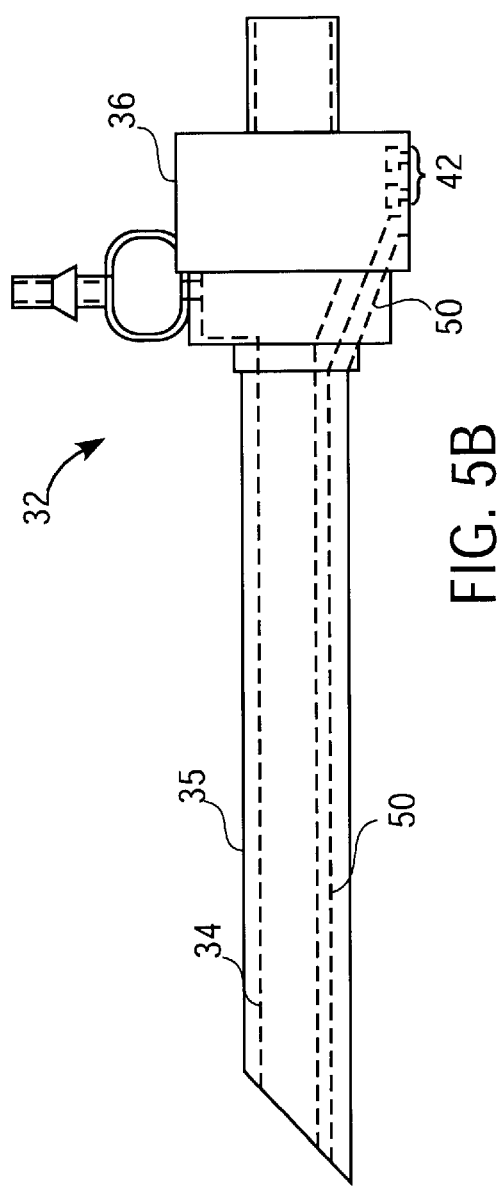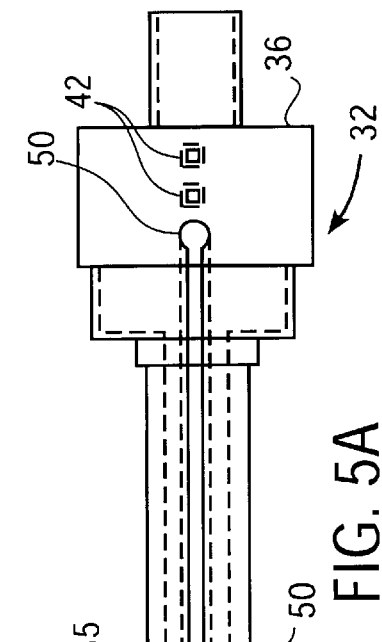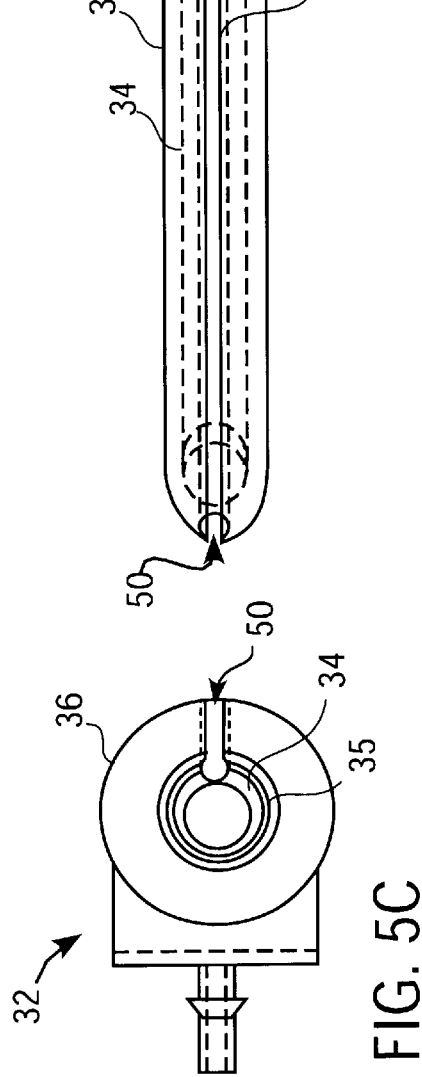
FIG. 5B
FIG. 5A
FIG. 5C

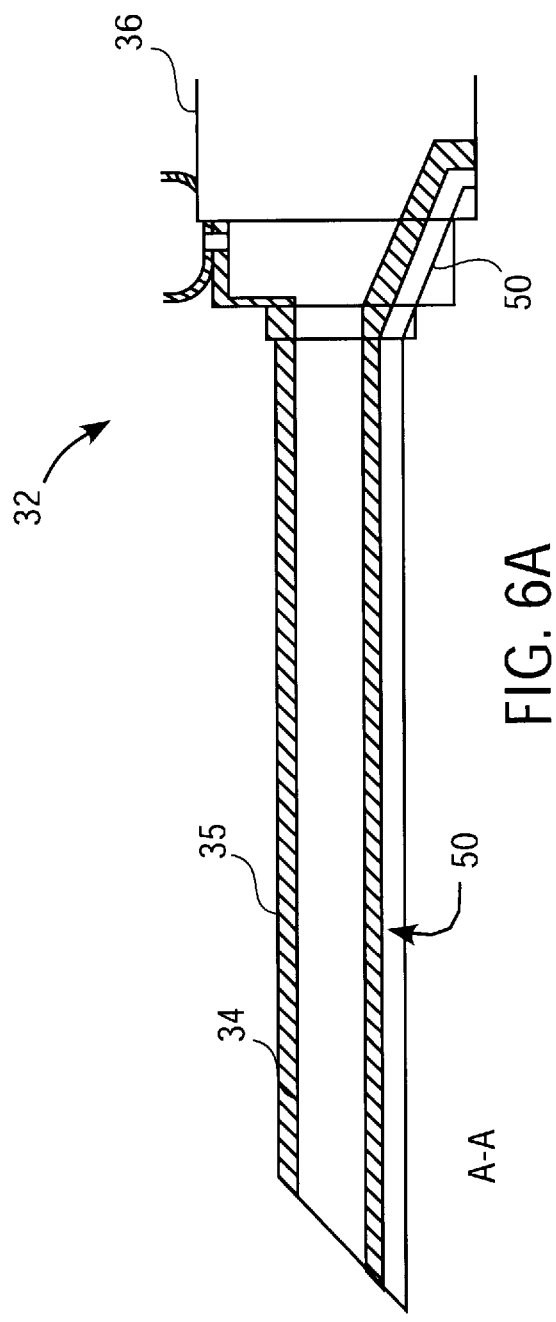
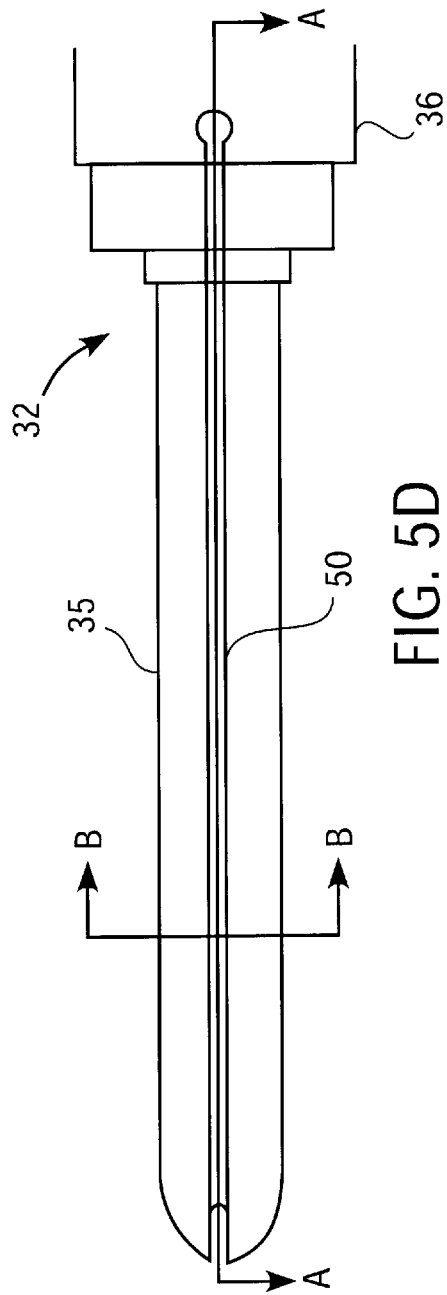
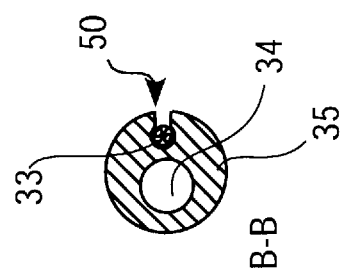
FIG. 6A
FIG. 5D
FIG. 6B

ENDOSCOPIC CAMERA SYSTEM INTEGRATED WITH A TROCAR SLEEVE

FIELD OF THE INVENTION

The present invention pertains to the field of endoscopic camera systems. More particularly, the present invention relates to a method and apparatus for integrating an endoscopic camera system with a trocar sleeve.

BACKGROUND OF THE INVENTION

Endoscopy is a medical field in which internal features of the body of a patient are viewed without the use of traditional (fully-invasive) surgery. Endoscopy is now widely used to perform minimally-invasive surgical procedures, such as arthroscopy and laparoscopy. A basic endoscopy tool is the endoscopic camera system, which includes a scope that is inserted into the body of a patient and a camera coupled to the scope. Images acquired by the camera are typically displayed on a conventional video monitor.

During endoscopic surgery, it is important for the surgeon to have an adequate view of the surgical area. However, endoscopic camera systems typically provide a very narrow field of view compared to the view the surgeon would have during traditional surgery. The narrow field of view can create difficulties during endoscopic surgery. For example, bleeding or other complications may occur outside the field the view, making it difficult for the surgeon to locate the source of such complications. The narrow field of view may also make it difficult for the surgeon to see all of the surgical tools and anatomical features in the surgical area without moving the scope. Further, tools used by a surgical assistant, such as a gripper, may not be within the immediate surgical area and therefore may not be visible within the field of view. This may make it difficult for the surgical assistant to make adjustments quickly and accurately in response to the surgeon's instructions, since the assistant has no visual feedback. Moreover, the limited field of view may hinder the use of an endoscopic camera system as an effective teaching or explanatory tool, since it may be difficult for students or other observers to visualize features outside the field the view.

SUMMARY OF THE INVENTION

The present invention includes a method and apparatus for integrating an endoscopic camera system with a trocar sleeve. This technique allows the endoscopic camera to be used as a secondary camera to provide a broad overview of a surgical area, which may be used to supplement the view provided by a main endoscopic camera.

Accordingly, one aspect of the present invention is an endoscope configured to be removably attached to a trocar sleeve.

Another aspect of the present invention is a trocar sleeve configured to accommodate an endoscopic camera system. The trocar sleeve includes a tube having a first end configured for insertion into the body of a patient. The tube has an inner surface which defines a channel for accommodating a surgical tool. The trocar sleeve further includes a receptacle configured to hold an endoscope.

Another aspect of the present invention is a trocar sleeve which comprises a tube and a base coupled to the tube. The base includes a fastener configured to allow removable attachment of an endoscopic camera head to the base.

Another aspect of the present invention is a camera head for endoscopic imaging. The camera head comprises image generation circuitry for generating image data based on light received through an endoscope and a housing enclosing the image generation circuitry. The housing includes a fastener configured to allow the housing to be removably attached to a trocar sleeve.

Another aspect of the present invention is a n endoscopic system which includes an endoscope and an endoscopic camera, both integrated with a trocar sleeve.

Other features of the present invention will be apparent from the accompanying drawings and from the detailed description which follows.

BRIEF DESCRIPTION OF THE DRAWINGS

The present invention is illustrated by way of example and not limitation in the figures of the accompanying drawings, in which like references indicate similar elements, and in which:

FIGS. 1A and 1B collectively illustrate an endoscopic camera system.

FIGS. 4A, 4B and 4C illustrates three orthogonal views of an endoscope configured to be integrated with a trocar sleeve.

FIGS. 5A, 5B and 5C illustrates three orthogonal views of a trocar sleeve configured to be integrated with an endoscopic camera and an endoscope.

FIG. 5D illustrates a partial view of the trocar sleeve showing a broadside view of the groove for holding an endoscope.

FIGS. 6A and 6B are cross-sectional views of the trocar sleeve corresponding to FIG. 5D.

DETAILED DESCRIPTION

Figures 2A, 2B, 2C:
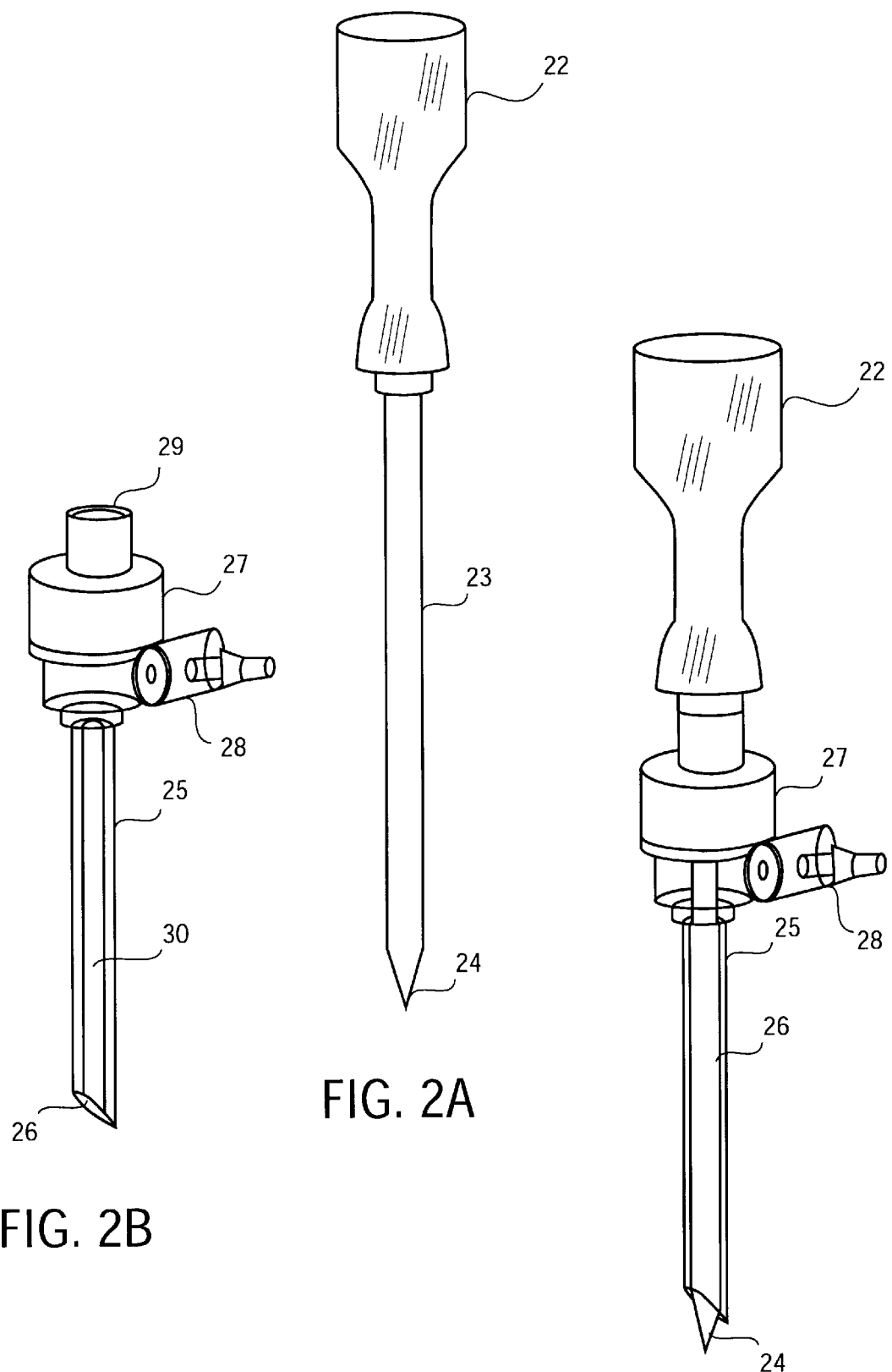
FIG. 2A illustrates a trocar.
FIG. 2B illustrates a trocar sleeve for use with the trocar of FIG. 2A.
FIG. 2C shows the trocar of FIG. 2A inserted into the trocar sleeve of FIG. 2B.

A technique for integrating an endoscopic camera system with a trocar sleeve is described. The described technique allows the integrated endoscopic camera to be used to provide a broad overview of a surgical area, which may be used to supplement the more narrow view provided by another endoscopic camera. The integrated camera system may be removed from the trocar sleeve to allow reuse of the camera system after proper sterilization.

FIGS. 1A and 1B collectively illustrate a typical, conventional endoscopic camera system. FIG. 1A generally illustrates the image generation and display components of the system, while FIG. 1B illustrates the data acquisition components of the system. Referring to FIG. 1B, the data acquisition components include an endoscope ("scope") 2, a camera 3, and a coupler 6 connecting the scope 2 to the camera 3. The illustrated scope 2 is a rigid scope of the type commonly used for laparoscopy or arthroscopy. The camera 3 acquires color video image data of internal features of a body through a system of lenses within the scope 2.

Referring to FIG. 1A, in the illustrated embodiment, the image generation and display components of the system include a camera control unit (CCU) 4, a light source unit 7, a monitor 9, a video cassette recorder (VCR) 10, and a printer 11, which are stored on a mobile cart 12. Light for acquiring images is provided to the scope 2 by light source unit 7 through an appropriate flexible light conduit 8, such as fiber optic cable. Operation of the camera system may be controlled from the CCU 4. The camera 3 is coupled to a camera control unit (CCU) 4 by a flexible transmission line 5. Transmission line 5 conveys video image data from the camera 3 to the CCU 4 and conveys various control signals bi-directionally between the camera 3 and the CCU 4. Image data received by the CCU 4 from the camera 3 are processed and converted to video images by the CCU 4, which are displayed on monitor 9, recorded in VCR 10, and/or used to generate static images that can be printed by printer 11.

In endoscopic surgery, an instrument known as a trocar is commonly used to penetrate tissue to create a portal into a body cavity for surgical instruments, such as an endoscope. FIG. 2A illustrates an example of a typical trocar, which includes a handle 22 and a shaft 23. The shaft 23 has a sharp tip 24 for penetrating tissue. The trocar is commonly used with a trocar sleeve, a typical example of which is shown in FIG. 2B, to penetrate the body cavity. In particular, the trocar is inserted into the trocar sleeve, as shown in FIG. 2C, and the two integrated devices are pushed through the wall of the body cavity together. The trocar is then removed from the trocar sleeve, and the trocar sleeve is left in place to serve as a channel (passageway) for surgical instruments, such as an endoscope. In general, both the trocar and the trocar sleeve are disposable.

Referring again to FIG. 2B, the trocar sleeve includes a hollow tube 25 and a base 27 coupled to the tube 25. In the illustrated trocar sleeve, the tube 25 is transparent, while the base 27 is opaque, as with many common trocar sleeves. The interior surface of the hollow tube 25 defines a channel 30 through which a surgical instrument, such as a trocar or endoscope, can pass, as shown in FIG. 2C. The trocar sleeve also includes a fluid control port 28 coupled to the base 27. An end 26 of the tube 25 is inserted into the body of the patient, as described above in connection with FIG. 2C. The base 27 has an opening 29. Enclosed within the base 27 is a valve (not shown), which allows an instrument to enter the tube 25 from opening 29 but prevents fluids from the body cavity from exiting through opening 29. Fluid control port 28 can be coupled to a fluid control system to control the flow of fluid into and out of the trocar sleeve for purposes of irrigating or draining the surgical area.

As noted, a trocar sleeve may be used to provide a channel into the body cavity for an endoscope. However, as noted above, the endoscope may provide and inadequate view of the surgical area. The present invention provides a solution to this problem by allowing a second endoscopic camera system to be used with the trocar sleeve, and more specifically, by allowing the second endoscopic camera system to be integrated with the trocar sleeve. The camera system that is integrated with the trocar sleeve may be used as a "secondary" endoscopic camera system to supplement the view provided by a main endoscopic camera system. For example, the secondary camera system may be used to provide a broad overview (i.e., a "bird's eye view") of the surgical area. The main endoscopic camera may be used in the conventional manner with the same trocar sleeve. It will be recognized that the described camera system integrated with a trocar sleeve does not have to be used in conjunction with another endoscopic camera system. Hence, for certain applications, the described camera system integrated with a trocar sleeve may be used alone or as a main endoscopic camera system.

Figure 3:
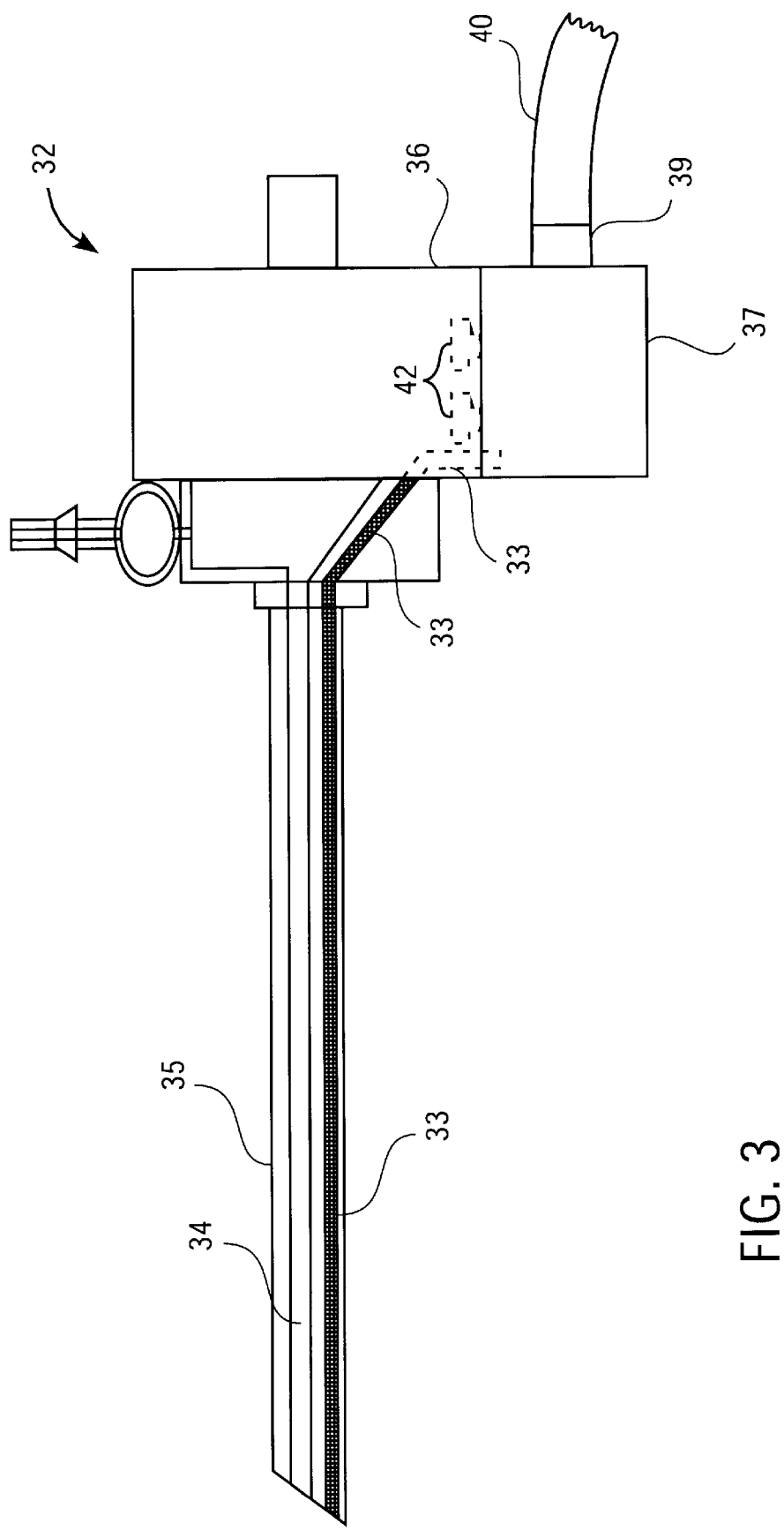
FIG. 3 illustrates an endoscopic camera and an endoscope integrated with a trocar sleeve.

FIG. 3 illustrates an endoscopic camera system integrated with a trocar sleeve 32, to allow its use as such a secondary camera system. The trocar sleeve 32 may be assumed to be essentially identical to the trocar sleeve described in connection with FIG. 2B, except as otherwise described herein or as will be otherwise apparent to those skilled in the art from this description. The integrated camera system includes a small diameter (e.g., 2.3 mm) scope 33 that is held securely within a receptacle of the trocar sleeve 32. In one embodiment, the receptacle is formed in both the tube 25 and the base 36, as will be described further below. Note, however, that the receptacle is not the main channel 34 of the tube 35 and base 36 through which surgical instruments are passed.

A miniature endoscopic camera head 37 including a small Charge-Coupled Device (CCD) array (e.g., ⅛ inch) is removably coupled to the base 36 and to the scope 33. The scope 33 is both physically and optically coupled to the camera head 37. The scope 33 is angled near the end closest to the base 36 to allow its connection to the camera head 37 at the exterior surface of the base 36. In the illustrated embodiment, the scope 33 protrudes slightly beyond the exterior surface of the base 36 to allow it to be connected to a corresponding connector (e.g., receptacle) on the camera head 37, and also to provide a place to grasp the scope 33, so that the scope 33 may be removed from the trocar sleeve 32. The camera head 37 is coupled to a CCU (such as CCU 4 or a separate CCU) via a standard S-video or other suitable video connector 39 and a conventional video transmission line 40.

The scope 33 and the camera head 37 may be removed from the trocar sleeve 32, such that these components can be reused after proper sterilization. The trocar sleeve 32 may be disposable.

FIGS. 4A, 4B and 4C illustrates three orthogonal views of the endoscope 33. The scope 33 includes an input end 43 designed to receive light from within the body cavity of the patient. A camera interface 41 at the other end of the scope 33 is designed for connection to a corresponding connector in the camera head 37. The scope 33 is angled at the end closest to the camera interface 41 to allow its connection to the camera head 37 at the exterior surface of the base 36, as noted above. In the embodiments shown, the scope 33 includes two bends that provide a total angular offset of 90 degrees. In other embodiments, however, the scope 33 may include a greater or smaller number of bends, which may provide a different angular offset, to accommodate trocar sleeves of different configurations.

FIGS. 5A, 5B and 5C Illustrates three orthogonal views of the trocar sleeve 32 according to one embodiment, To facilitate description, the trocar sleeve 32 is shown completely opaque in FIGS. 5A, 5B and 5C, with broken lines representing certain internal structure. Note, however, that the valve of trocar sleeve 32 is not germane to the present invention and is therefore not shown. In the illustrative embodiment, the above-mentioned receptacle which receives the scope 33 is a groove 50 formed in both the tube 35 and the base 36. FIG. 5A illustrates a view looking directly into the groove 50 broadside. FIG. 5B illustrates a side view corresponding to the view of FIG. 3. As shown, the groove 15 passes through the base 36 in a path that matches the shape of scope 33. The groove 50 is sized and shaped appropriately so that the endoscope 33 can snap into place and be held securely, yet can be easily removed. As shown in FIGS. 5A, 5B and 5C, the groove 50 is separate from the channel 34 through which a trocar, main endoscope, or other instruments are passed. The trocar sleeves of the present invention may be constructed of the same well-known materials of which conventional trocar sleeves are constructed.

FIG. 5D illustrates a partial view of the trocar sleeve 32 looking broadside into the groove 50 (without broken lines for the internal structure). FIGS. 6A and 6B are the cross-sectional views represented in FIG. 5D. In particular, FIG. 6A is a partial cross-sectional view showing the length of the tube 35. FIG. 6B is a cross-sectional view showing the diameter of the tube 35, viewed from the end of the tube 35 that is inserted into the patient. Although not shown in FIG. 5D, the scope 33 is shown in FIG. 6B (also in cross-section) disposed within the groove 50, to further illustrate how a scope may be integrated with the trocar sleeve 32.

Figure 7:
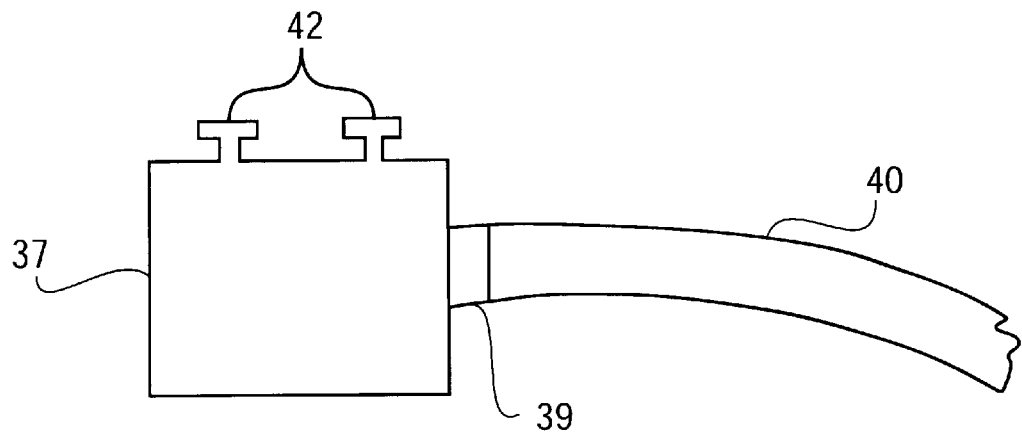
FIG. 7 illustrates an endoscopic camera head configured to be integrated with a trocar sleeve.

FIG. 7 further illustrates the miniature camera head 37, which includes a fastener 42 that mates with a corresponding fastener in the base 36 of the trocar sleeve 32, as shown in FIG. 3. Fastener 42 and its counterpart in the base 36 each may be any type of fastener that is suitable for allowing quick and easy attachment and removal of the camera head 37 from the base 36, such as a conventional snap-on fastener.

Figure 8:
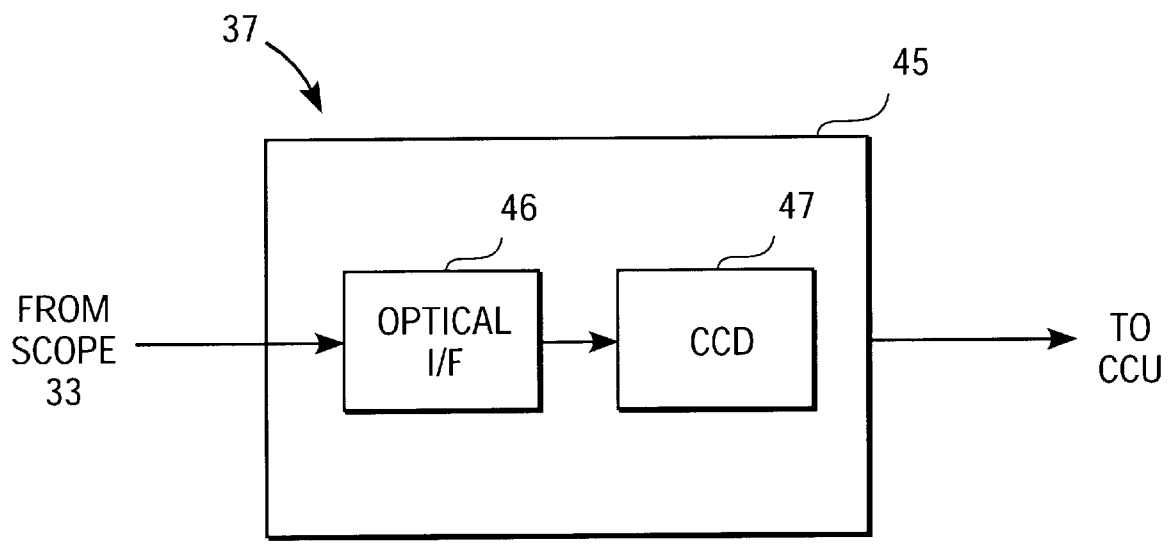
FIG. 8 is a block diagram of the endoscopic camera head.

FIG. 8 is a block diagram showing the major components of the camera head 37. Contained within the housing 45 of the camera head 37 are an optical interface 46 and a CCD array 47. The optical interface 46 receives light input from the camera interface 41 of the scope 33. The optical interface 46 may include one or more prisms and/or filters, such as are well-known in the art. Light output by the optical interface 46 is provided to the CCD array 47, which outputs corresponding electrical signals to a CCU via the connector 39 and transmission line 40. The electrical signals output by the CCD array 47 may undergo further processing within the camera head 37 prior to transmission to the CCU, the nature of which is not germane to the present invention.

Figure 9:
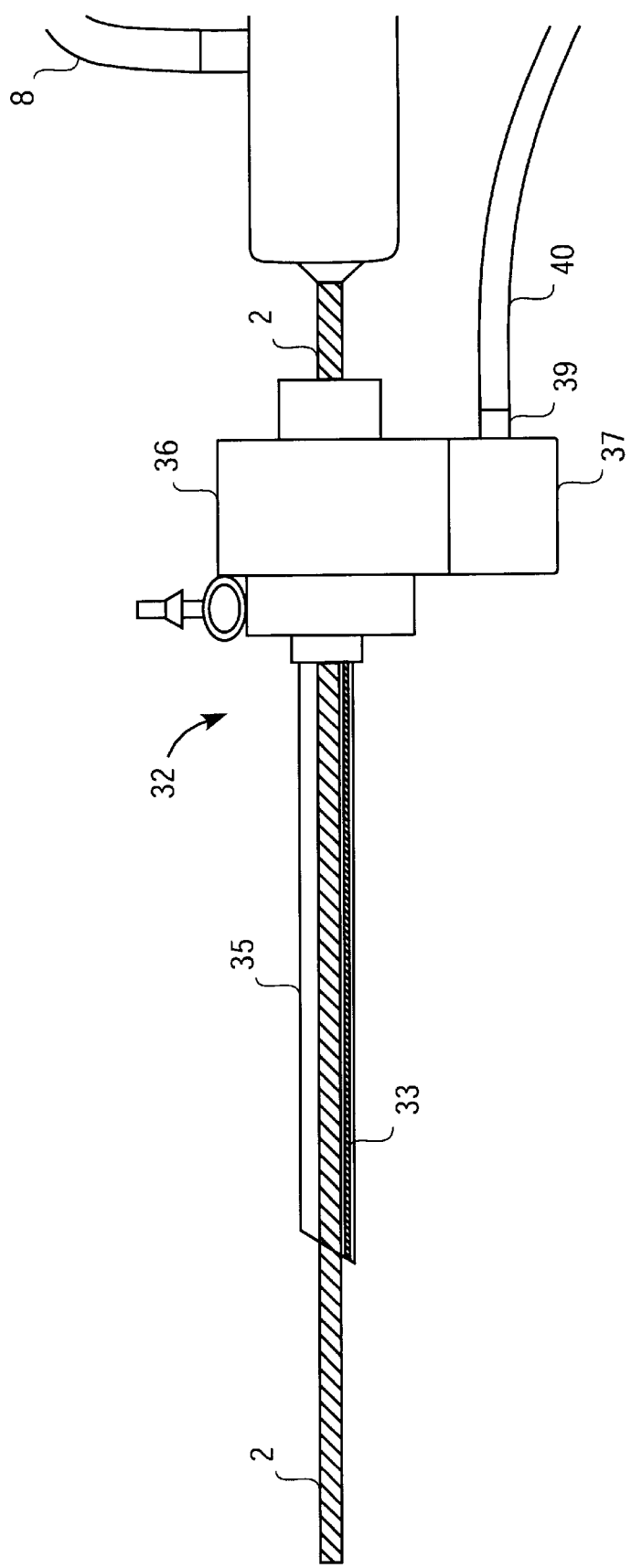
FIG. 9 illustrates a manner of using a trocar sleeve with a secondary endoscopic camera system integrated therein, and with a main endoscope inserted in the same trocar sleeve.

FIG. 9 illustrates how the above-described trocar sleeve 32 may be used to hold an integrated secondary endoscopic camera system, with the main endoscope inserted in the same trocar sleeve 32. It will be recognized, however, that a separate trocar sleeve may be used for the main camera system, if desired. As shown, the secondary camera system, which includes scope 33, camera head 37 and transmission line 38, is integrated with the trocar sleeve 32 in the manner described above. The scope 2 of the main endoscopic camera system is inserted through the main channel 34 (see FIGS. 3, 5A, 5B and 5C) of the trocar sleeve 32 in the conventional manner. The scope 2 of the main endoscopic camera system is much longer than the tube 35 and therefore extends well beyond the end of the tube 35. In contrast, the secondary scope 33 preferably extends only to the end of the tube 35, as shown, or if desired, slightly beyond or short of the end. The length of the scope 33 may be chosen appropriately with this application in mind during the design process. Because the tip of the scope 33 is located farther from the surgical area than the tip of the main scope 2, the area included within the field of view of the secondary camera system is generally wider than that viewed by the main camera system. Further, the scope 33 may be designed to have an inherently wider field of view with this application in mind. For example, the scope 33 may include a "short-optical" system for this purpose.

Thus, the secondary camera system integrated with the trocar sleeve can be used to provide the surgeon with a broad overview of the surgical area, including any equipment that the surgeon's assistant is manipulating. This technique can be useful in quickly identifying and locating complications, such as bleeding, originating in locations outside the field of view of the main camera system. Further, this technique provides the surgeon with an improved sense of orientation of his instruments within the surgical field. Additionally, a secondary camera system according to this technique can be used as a teaching or explanatory tool for new surgeons or other observers. Again, the above-described camera system integrated with a trocar sleeve need not be used as a secondary camera system; that is, it may be used alone or as the main endoscopic camera system, if desired.

Figure 10:
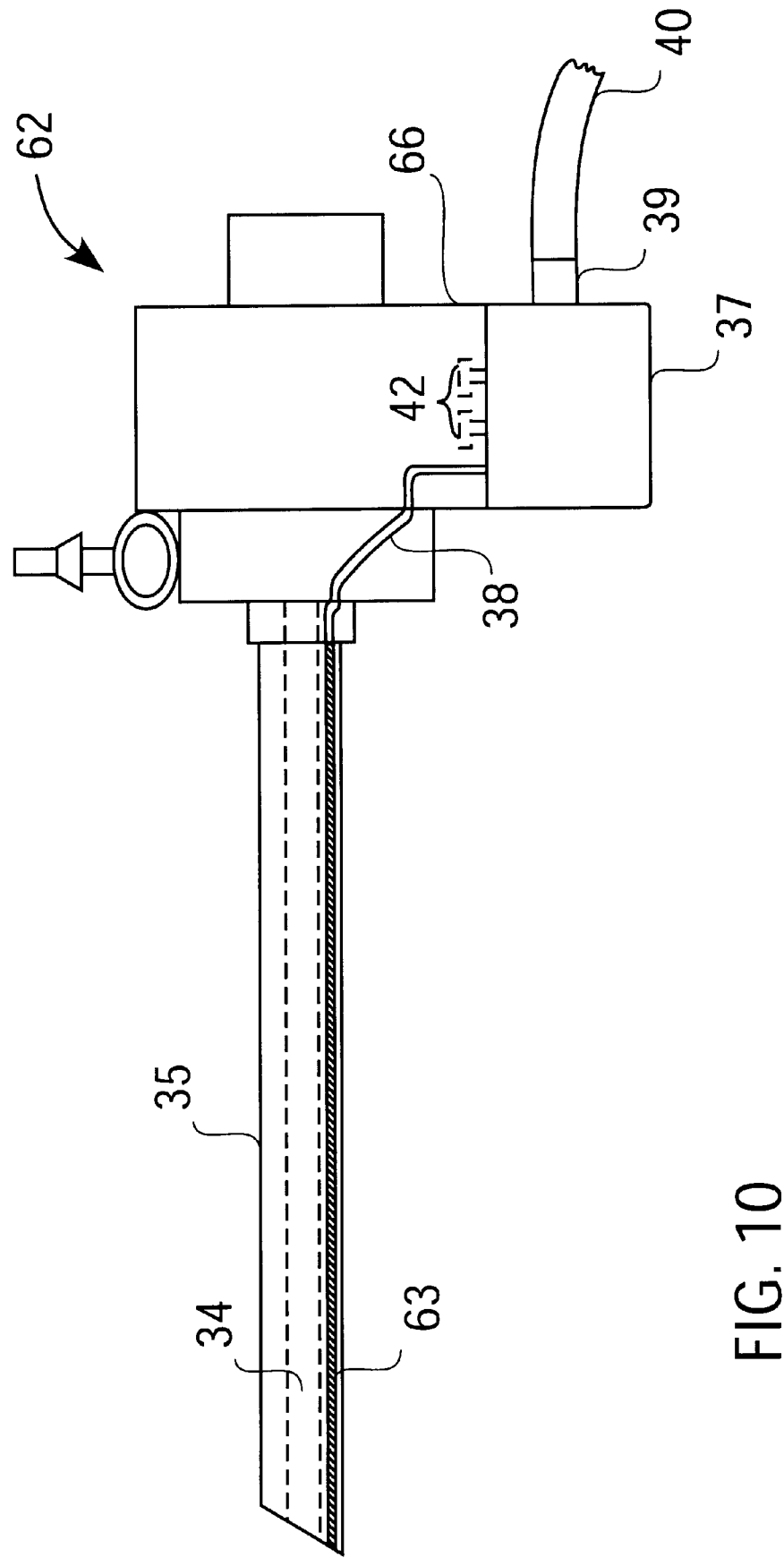
FIG. 10 illustrates an endoscopic camera and a straight endoscope integrated with a trocar sleeve, wherein the camera and the endoscope are connected by an optical transmission line.

FIG. 10 illustrates an endoscopic camera head and scope integrated with a trocar sleeve 62, in accordance with an alternative embodiment. In this alternative embodiment, a straight scope 63 is used, rather than an angled scope of the type illustrated in FIGS. 4A, 4B and 4C. Further, an optical transmission line 38 optically couples the scope 63 to the camera head 37. The optical transmission line 38 may consist of, for example, flexible fiber optic cable or a series of rod lenses and/or prisms. In various embodiments, the transmission line 38 may be located either within the base 66 of the trocar sleeve 60 or external to the base 66. Similarly, in various embodiments, the transmission line 38 may be attached to the base 66 or not attached to the base 66. In some embodiments, the trocar sleeve 62 may be manufactured with the transmission line 38 built into the base 66, with appropriate connectors provided for the scope 63 and the camera head 37.

Thus, a technique for integrating an endoscopic camera system with a trocar sleeve has been described. Although the present invention has been described with reference to specific exemplary embodiments, it will be evident that various modifications and changes may be made to these embodiments without departing from the broader spirit and scope of the invention as set forth in the claims. Accordingly, the specification and drawings are to be regarded in an illustrative sense rather than a restrictive sense.

What is claimed is:

1. A trocar sleeve comprising:
   tubular member;
   a first channel formed by an inner surface of the tubular member to accommodate a surgical tool; and
   a second channel, separate from the first channel, formed by an outer surface of the tubular member, to allow removable insertion of an endoscope into the trocar sleeve.

2. A trocar sleeve as recited in claim 1, further comprising a base coupled to an end of the tubular member.

3. A trocar sleeve as recited in claim 2, further comprising a continuation of second channel formed in an outer surface of the base, to allow removable insertion of the endoscope into the trocar sleeve.

4. A trocar sleeve as recited in claim 2, wherein the base includes a fastener configured to allow removable coupling of an endoscopic camera head to the base.

5. A trocar sleeve as recited in claim 1, wherein the second channel is defined lengthwise along the outer surface of the tubular member.

6. A trocar sleeve as recited in claim 1, wherein the endoscope is a rigid endoscope.

7. A trocar sleeve comprising:

a tubular member having an inner surface forming a channel to accommodate a surgical tool;

a groove, a first segment of which is defined lengthwise in an outer surface of the tubular member to allow removable insertion of a rigid endoscope into the tubular member, such that at least a portion of the rigid endoscope is disposed substantially parallel to the channel when inserted into the tubular member; and a base coupled to the tubular member and having a second segment of the groove defined therein, to accommodate a portion of the rigid endoscope when the endoscope is inserted into the tubular member.

8. A trocar sleeve as recited in claim 7, wherein the base includes a fastener configured to allow removable coupling of an endoscopic camera head to the trocar sleeve.

9. An apparatus comprising:

a tubular member having a first end configured for insertion into the body of a patient, the tubular member further having an inner surface defining a channel for accommodating a surgical tool, the tubular member further having an outer surface with a groove defined lengthwise in the outer surface; and a base coupled to a second end of the tubular member opposite the first end, the base including a fastener configured to allow removable attachment of an endoscopic camera head to the base, the base further having an outer surface with a continuation of said groove defined in the outer surface of the base, such that a rigid endoscope can be removably inserted into said groove.

10. A trocar sleeve comprising:

a tube having a first end configured to allow insertion into the body of a patient, the tube further having an inner surface defining a channel to accommodate an inserted trocar, the tube further having an outer surface with a groove defined lengthwise therein; and a base coupled to a second end of the tube opposite the first end, the base including a fastener configured to allow removable attachment of an endoscopic camera head to the base, the base further having an outer surface with a continuation of said groove defined in the outer surface of the base, the groove configured to allow removable attachment of a rigid endoscope to the trocar sleeve, such that at least a portion of the rigid endoscope is disposed substantially parallel to the channel when inserted into the tubular member.

11. An endoscope comprising:

an input interface to receive light reflected from a body to be viewed;

an output interface to couple the endoscope to an endoscopic camera; and a rigid elongate member to transmit light from the input interface to the output interface, the elongate member having at least one bend to conform the endoscope to a shape of a trocar sleeve.

12. An endoscope as recited in claim 11, such that the endoscope is removably insertable into a channel defined in an outer surface of the trocar sleeve.

13. An endoscope as recited in claim 11, wherein the at least one bend provides a total angular offset of approximately 90 degrees.

14. An endoscope comprising:

input interface to receive light;

an output interface to couple the endoscope to an endoscopic camera; and a rigid elongate member to transmit light from the input interface to the output interface, the elongate member having at least one bend to conform the endoscope to a shape of a trocar sleeve, such that the endoscope can be removably inserted into a groove defined in an outer surface of the trocar sleeve.

15. An endoscope as recited in claim 14, wherein the at least one bend provides a total angular offset of approximately 90 degrees.

* * * * *